US005567713A

United States Patent [19]

Cullinan et al.

[11] Patent Number: 5,567,713
[45] Date of Patent: Oct. 22, 1996

[54] HYPOGLYCEMIC AGENTS

[75] Inventors: George J. Cullinan, Trafalgar; Terence T. Yen, Indianapolis, both of Ind.

[73] Assignee: Eli Lilly and Company, Indianapolis, Ind.

[21] Appl. No.: 370,062

[22] Filed: Jan. 9, 1995

Related U.S. Application Data

[62] Division of Ser. No. 82,218, Jun. 24, 1993, abandoned.
[51] Int. Cl.⁶ .......................... A61K 31/445; A61K 31/40
[52] U.S. Cl. ........................................ 514/324; 514/422
[58] Field of Search .................................. 514/324, 422

[56] References Cited

U.S. PATENT DOCUMENTS

| | | | |
|---|---|---|---|
| 2,914,563 | 11/1959 | Allen et al. | 514/324 |
| 3,274,213 | 9/1966 | Lednicer et al. | 514/324 |
| 4,133,814 | 1/1979 | Jones et al. | 514/324 |
| 4,230,862 | 10/1980 | Suarez et al. | 514/324 |
| 4,323,707 | 4/1983 | Suarez et al. | 514/324 |
| 4,400,543 | 8/1983 | Suarez et al. | 514/324 |
| 4,418,068 | 11/1983 | Jones | 514/324 |
| 4,536,516 | 8/1985 | Harper et al. | 514/324 |
| 4,729,999 | 3/1988 | Young | 514/324 |
| 4,894,373 | 1/1990 | Young | 514/324 |
| 4,970,237 | 11/1990 | Jensen et al. | 514/324 |

FOREIGN PATENT DOCUMENTS

| | | | |
|---|---|---|---|
| 470310 | 2/1992 | European Pat. Off. | 514/324 |
| 509317 | 10/1992 | European Pat. Off. | 514/324 |

OTHER PUBLICATIONS

Williams, et al., *Journal of Bone and Mineral Research*, 6 (1991).
*FDC Reports*, T&G 11, Mar. 30, 1992.
Jones, et al., *J. Med. Chem.*, 27, 1057–1066 (1984).
Feldmann, et al., *Bone and Mineral*, 7, 245–254 (1989).
"Tamoxifen Trial Restricted", *SCRIP* No. 1702 Mar. 20, 1992, p. 22.
Jordan, et al., *Breast Cancer Research Treatment*, 10:31–35 (1987).
Beall, et al., *Calcif Tissue Int.*, 36: 123–125 (1984).
Turner, et al., *Journal of Bone and Mineral Research*, 2, No. 5, 449–456 (1987).
Williams, et al., *Bone and Mineral*, 14, 205–220 (1991).
Turner, et al., *Endocrinology*, 122, No. 3, 1146–1150 (1988).
Love, et al., *The New England Journal of Medicine*, 326, No. 13, 852–856 (1992).
Breckenridge, et al., *Lipids*, 22, No. 7, 505–512 (1987).
Lazier, et al., *Biochem. Cell Biol.*, 68, 210–217 (1990).
Lobo, *J. Clin. Endocrinol. Metab.*, 73, No. 5, 925–930 (1991).
Love, et al., *Ann. Intern. Med.*, 115, No. 11, 860–864 (1991).
Walsh, et al., *N. Engl. J. Med.*, 325, No. 17, 1196–1204 (1991).
Bagdade, et al., *J. Clin. Endocrinol. Metab.*, 70, No. 4, 1132–1135 (1990).
Love, et al., *J. Natl. Cancer Inst.*, 82, No. 16, 1327–1332 (1990).
Teo, et al., *J. Med. Chem.*, 35, 1330–1339 (1992).
Cypriani, et al., *J. Steroid Biochem.*, 31, No. 5, 763–771 (1988).
Cypriani, et al., *Chemical Abstracts*, CA 110: 1189 v, 1989.
Cypriani, et al., *Chemical Abstracts*, 110:69550v, 1989.
American Chemical Society, *Registry*, RN# 63676-25-5 (1985).
Nishino, et al., *J. of Endocrinology*, 130, 409–414 (1991).
Wakeling, et al., *J. of Endocrinology*, 112, R7–R10 (1987).
Arai, et al., *Jpn. J. Vet. Sci.*, 51, 823–826 (1989).
Dubuc, *Proc. Soc. Exp. Biol. Med.*, 180, 468–473 (1985).
Garris, *Anat. Rec.*, 225, 310–317 (1989).
Cagnacci, et al., *J. Clin. Endocrinol. Metab.*, 74, 1396–1400 (1992).
Saeed, et al., *J. Med. Chem.*, 33, 3210–3216 (1990).
Sharma, et al., *J. Med. Chem.*, 33, 3216–3222 (1990).
Sharma, et al., *J. Med. Chem.*, 33, 3222–3229 (1990).
Ogawa, et al., *Chem. Pharm. Bull.*, 39, 911–916 (1991).
von Angerer, et al., *J. Med. Chem.*, 33, 2635–2640 (1990).
Teo, et al., *J. Chem. Reearch* (5), 4–5 (1990).
Draper, et al., Abstract for Presentation at 4th International Symposium on Osteoporosis and Consensus Development Conference, Hong Kong, Mar. 27, 1993.
Bjorntorp, *Ann. N.Y. Acad. Sci*, 676, 242–252 (1993).
Wade, et al., *Am. J. Physiol*, 264 (Regulatory Integrative Comp. Physiol. 33): R1219–R1223 (1993).
Gray, et al., *Am. J. Physiol.*, 264 (Regulatory Integrative Comp. Physiol. 33): R1214–R1218 (1993).
Gray, et al., *Am. J. Physiol.*, 243, (Endocrinol. Metab. 6): E407–E412 (1992).
Gray, et al., *Am. J. Physiol.*, 240 (Endocrinol. Metab. 3): E474–E481 (1981).

*Primary Examiner*—Jerome D. Goldberg
*Attorney, Agent, or Firm*—James J. Sales; John C. Demeter; David E. Boone

[57] ABSTRACT

The present invention provides a method for treating hyperglycemia in mammals by administering an antiestrogen compound and pharmaceutically acceptable salts and solvates thereof.

4 Claims, No Drawings

HYPOGLYCEMIC AGENTS

This application is a division, of application Ser. No. 08/082,218, filed Jun. 24, 1993 now abandoned.

BACKGROUND OF THE INVENTION

Diabetes mellitus is a systemic disease characterized by disorders in the actions of insulin and other regulatory hormones in the metabolism of carbohydrates, fats and proteins, and in the structure and function of blood vessels. The primary symptom of diabetes is hyperglycemia, often accompanied by glucosuria, the presence in urine of large amounts of glucose, and polyurea, the excretion of large volumes of urine. Additional symptoms arise in chronic or long standing diabetes. These symptoms include degeneration of the walls of blood vessels. Although many different organs are affected by these vascular changes, the nerves, eyes and kidneys appear to be the most susceptible. As such, long-standing diabetes mellitus, even when treated with insulin, is a leading cause of blindness.

There are two recognized types of diabetes. Type I diabetes is of juvenile onset, ketosis-prone, develops early in life with much more severe symptoms and has a near-certain prospect of later vascular involvement. Control of this type of diabetes is difficult and requires exogenous insulin administration. Type II diabetes mellitus, is of adult onset, ketosis-resistant, develops later in life, is milder and has a more gradual onset.

One of the most significant advancements in the history of medical science came in 1922 when Banting and Best demonstrated the therapeutic effects of insulin in diabetic dogs. However, even today, a clear picture of the basic biochemical defects of the disease is not known, and diabetes remains a serious health problem. It is believed that two percent of the United States population is afflicted with some form of diabetes. The introduction of orally effective hypoglycemic agents was an important development in the treatment of hyperglycemia. Oral hypoglycemic agents are normally used in the treatment of adult onset diabetes.

Observations in animal models on glucose metabolism for type II diabetes and in humans suggest that sex steroids play a permissive role in the phenotypic expression of hyperglycemia. These observations have prompted studies on the effects of androgens and estrogens on blood glucose levels. Testosterone administration to intact or ovarectomized female rats resulted in marked insulin resistance which correlated to morphological changes in muscle, Holmang, et al., *Am. J. Physiol.*, 259, E555–560 (1990); Holmang, et al., *Am. J. Physiol.*, 262, E851–855 (1992). In streptozotocin diabetic rats, implanted testosterone antagonized the ability of residual insulin to maintain glycemic control, Leet al., *Endocrinology*, 116, 2450–2455 (1985). In contrast, glucosuria disappeared in castrated diabetic KK mice and reappeared when androgens were replaced in these mice, Nonaka, et al., *Jpn. J. Vet. Sci.*, 50, 1121–1123 (1988); Higuichi, et al., *Exp. Anim.*, 38, 25–29 (1989).

Results from estrogen administrations also support the hypothesis that the balance between androgens and estrogens is critical to the development of hyperglycemia. Daily estradiol administrations to diabetic KK mice normalized the blood glucose levels and eliminated glucosuria, Toshiro, et al., *Jpn. J. Vet. Sci.*, 51, 823–826 (1989). Estradiol also lowered the blood glucose levels of C57BL/6J-ob/ob mice, Dubuc, *Proc. Soc. Exp. Biol. Med.*, 180, 468–473 (1985) and C57BL/KsJ-db/db mice, Garris, *Anatomical Record*, 225, 310–317 (1989).

Sexual dimorphism of hyperglycemia was observed in VY/WfL-$A^{vy}$/a mice (VY mice, Shafrir, Ed., *Lessons From Animal Diabetes, III*, 294–299, Smith-Gordon, London (1990); Gill, et al., *Life Sci.*, 48, 703–710 (1991). However, hyperglycemia could be induced by dexamethasone (dex) in female VY mice, Yen, et al., *Int. J. Obesity*, 16, 923–933 (1992).

The present invention relates to methods of lowering blood glucose levels in mammals by administering to a mammal in need of treatment, an effective amount of an antiestrogen. These compounds may be useful for treating diabetes. Other objects, features and advantages of the present invention will become apparent from the subsequent description and the appended claims.

SUMMARY OF THE INVENTION

The present invention provides a method of reducing blood glucose concentrations in mammals in need of blood glucose concentration reduction comprising administering a therapeutically effective amount of an antiestrogen compound or a pharmaceutically acceptable salt or solvate thereof.

DETAILED DESCRIPTION OF THE INVENTION

The method of this invention is practiced by administering to a mammal in need of treatment, a therapeutically effective amount of an antiestrogen compound or a pharmaceutically acceptable salt or solvate thereof, preferably in a pharmaceutical formulation.

The phrase "antiestrogen" as used in this specification and claims means a non-endogenous, non-steroid chemical compound that demonstrates substantial antiestrogenic activity (as further defined below), but at the same time demonstrates hormonal or estrogenic activities in certain selective tissues or organs. Historically, the literature refers to antiestrogens as compounds which both bind to the estrogen receptor, (i.e., compete with estradiol for its receptor), and inhibit the response of the uterus or breast to estrogen, in vivo. Many of these compounds were shown to be useful as antifertility agents, anticancer agents, or other pathologies where the inhibition of estrogenic activity was beneficial. Many of these compounds were noted to be mixed agonist-antagonists, i.e., at certain dose levels behaved as estrogen agonist, while at higher doses were antagonists to estrogen. Methods of determining classical antiestrogens are well known to those skilled in the art, e.g., Hayes, J. R., et al., *J.A. Endocrinology*, 1981, 108, 164–172 and references therein.

Recently, it has been discovered that certain chemical classes of historically defined antiestrogens have the ability to act on certain estrogen responsive tissues or organs in a beneficial manner while antagonizing an estrogenic response in others. It is not clear whether this differential can be explained by a quantitative mixed agonist-antagonist action or that a qualitatively different mechanism is responsible. An example of this beneficial, differential response has been demonstrated with Raloxifene in its ability to lower serum lipids and to decrease bone resorption substantially without unwanted uterine effects in post-menopausal women.

It should be noted that not all compounds, which may be antiestrogens as defined by the classical definition as stated above, may possess the activity and utility described in this invention.

In general, antiestrogen compounds claimed in this invention are those compounds which are antiestrogenic in the classical sense, but which possess beneficial estrogenic properties. The most familiar compounds are of the chemical class of triarylethylene or (Z) triarylpropenone amines. Other antiestrogen chemical classes inclusion is based on their merits.

The preferred and most preferred compounds of this invention are those which demonstrate the greatest hypoglycemic effects, but which also demonstrate the least undesirable estrogenic side-effects in organs such as the breast and uterus. Jones, C. D., etal., *J. Hed. Chem.*, 1984, 27, 1057–1066. Additionally, the preferred compounds of this invention which have greatly reduced estrogen agonist activity would be most useful in the treatment of male patients to avoid feminizing side-effects such as gynecomastia.

The antiestrogens contemplated as within the scope of the present invention are those having an apparent binding affinity for the estrogen receptor, typically reported as Ki values of from greater than about 0.05 nanomolar to less than about 5000 nanomolar calculated from inhibitor $IC_{50}$ values using the equation $Ki=IC_{50}/[1+(L/Kd)]$ where L is the radioligand concentration and Kd is the dissociation contant of the ligand receptor complex determined by saturation studies or from the inhibition by the cold ligand for its own binding.

Procedures for performing binding assays to determine antiestrogenic and estrogenic activity are known to those skilled in the art. For example Black and Goode, *Life Sciences*, 26, 1453–1458 (1980); Black and Goode, *Endocrinology*, 199, 987–989 (1981); and Black, etal., *Life Sciences*, 32, 1031–1036 (1983.) Similarly, the relationship between apparent (or relative) binding affinity Hi as a function of inhibitor $IC_{50}$ values, radioligand concentration and dissociation of the ligand receptor complex as described in the above formula is also known to those skilled in the art.

The preferred method of determining estrogenic/antiestrogenic activities are according to procedures described below.

The following classes of antiestrogens have been reported and are believed useful in the methods of the present invention; 1) triarylethylenes; 2) 2,3-diaryl-2H-1-benzopyrans; 3) 1-aminoalkyl-2-phenylindoles; 4) 2-phenyl-3-aroylbenzothiophenes; 5) 1-substituted-2-aryl-dihydronaphthalenes; and 6) 2-substituted-3-aryl-benzofurans. Each of these classes is described below in greater detail.

The general chemical terms used in the description of the compounds of this invention have their usual meanings. For example, the term "alkyl" by itself or as part of another substituent means a straight or branched chain alkyl radical having the stated number of carbon atoms such as methyl, ethyl, propyl, and isopropyl and higher homologues and isomers where indicated.

The term "alkoxy" means an alkyl group having the stated number of carbon atoms linked to the parent moiety by an oxygen atom, such as methoxy, ethoxy, propoxy, butoxy, pentytoxy, and hexyloxy and also includes branched chain structures such as, for example, isopropoxy and isobutoxy.

The term "$C_1$–$C_7$-alkanoyloxy" means a group —O—C(O)—$R^a$ where $R^a$ is hydrogen or $C_1$–$C_6$ alkyl and includes formyloxy, acetoxy, propanoyloxy, butanoyloxy, pentanoyloxy, hexanoyloxy, and the like and also includes branched chain isomers such as, for example, 2,2-dimethylpropanoyloxy, and 3,3-dimethylbutanoyloxy.

Analogously, the term "$C_4$–$C_7$ cycloalkanoyloxy" means a group —O—C(O)—($C_3$–$C_6$ cycloalkyl) where the $C_3$–$C_6$ alkyl group includes cyclopropyl, cyclobutyl, cyclopentyl and cyclohexyl.

The term "($C_1$–$C_6$-alkoxy)-$C_1$–$C_7$-alkanoyloxy" means a group —O—C(O)—$R^b$—O—($C_1$–$C_6$ alkyl) where $R^b$ is a bond ($C_1$–$C_6$ alkoxycarbonyloxy) or $C_1$–$C_6$ alkanediyl and includes, for example, methoxycarbonyloxy, ethoxycarbonyloxy, propoxycarbonyloxy, butoxycarbonyloxy, methoxyacetoxy, methoxypropanoyloxy, methoxybutanoyloxy, methoxy-pentanoyloxy, methoxyhexanoyloxy, ethoxyacetoxy, ethoxypropanoyloxy, ethoxybutanoyloxy, ethoxypentanoyloxy, ethoxyhexanoyloxy, propoxyacetoxy, propoxypropanoyloxy, propoxybutanoytoxy, and the like.

The term "unsubstituted or substituted aroyloxy" means a group —O—C(O)-aryl where aryl is a phenyl, naphthyl, thienyl or furyl group that is, as to each group, unsubstituted or monosubstituted with a hydroxyl, halo, $C_1$–$C_3$ alkyl, or $C_1$–$C_3$ alkoxy.

The term "unsubstituted or substituted aryloxycarbonyloxy" means a group —O—C(O)—O-aryl where aryl is a phenyl, naphthyl, thienyl or furyl group that is, as to each group, unsubstituted or monosubstituted with a hydroxyl, halo, $C_1$–$C_3$ alkyl or $C_1$–$C_3$ alkoxy.

The term "halo" means chloro, fluoro, bromo or iodo.

The term "pharmaceutically acceptable salts" refers to salts of the compounds of the above classes which are substantially non-toxic to living organisms. Typical pharmaceutically acceptable salts include those salts prepared by reaction of a compound of the above class with a pharmaceutically acceptable mineral or organic acid, or a pharmaceutically acceptable alkali metal or organic base, depending on the types of substituents present on the compound.

Examples of pharmaceutically acceptable mineral acids which-may be used to prepare pharmaceutically acceptable salts include hydrochloric acid, phosphoric acid, sulfuric acid, hydrobromic acid, hydriodic acid, phosphorous acid and the like. Examples of pharmaceutically acceptable organic acids which may be used to prepare pharmaceutically acceptable salts include aliphatic mono and dicarboxylic acids, oxalic acid, carbonic acid, citric acid, succinic acid, phenyl-substituted alkanoic acids, aliphatic and aromatic sulfonic acids and the like. Such pharmaceutically acceptable salts prepared from mineral or organic acids thus include hydrochloride, hydrobromide, nitrate, sulfate, pyrosulfate, bisulfate, sulfite, bisulfite, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like.

Many compounds of the above classes which contain a carboxy, carbonyl, hydroxy or sulfoxide group may be converted to a pharmaceutically acceptable salt by reaction with a pharmaceutically acceptable alkali metal or organic base. Examples of pharmaceutically acceptable organic bases which may be used to prepare pharmaceutically acceptable salts include ammonia, amines such as triethanolamine, triethylamine, ethylamine, and the like. Examples of pharmaceutically acceptable alkali metal bases included compounds of the general formula MOZ, where M represents an alkali metal atom, e.g. sodium, potassium, or lithium, and Z represents hydrogen or $C_1$–$C_4$ alkyl.

It should be recognized that the particular anion or cation forming a part of any salt of this invention is not critical, so long as the salt, as a whole, is pharmacologically acceptable and as long as the anion or cationic moiety does not contribute undesired qualities.

In addition, some of the compounds disclosed as useful in the methods of the present invention may form solvates with water or common organic solvents. Such solvates are included within the scope of the present invention.

The first class of antiestrogens comprises triarylethylenes. These compounds are widely known and are disclosed in and prepared according to procedures described in U.S. Pat. No. 4,536,516; U.S. Pat. No. 2,914,563; Ogawa, et al., *Chem. Pharm, Bull*, 39(4), 911 (1991) which are all incorporated by reference herein, in their entirety. Specific illustrative compounds within this class include Tamoxifene, Clomiphene and (Z) -4-[1-[4-[2-dimethylamino)ethoxy] phenyl]-2-(4-isopropylphenyl)-1-butenyl]phenyl monophosphate.

The triarylethylenes include compounds having the formula

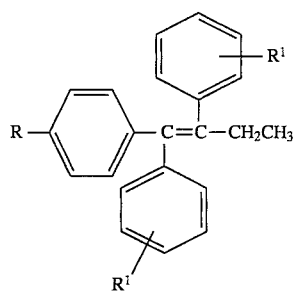

I where R is a basic ether group of the formula —$OC_nH_{2n}A$ where n is 2, 3 or 4 and A is a dialkylamino group where the alkyl groups independently contain from 1 to 4 carbon atoms or a cyclic structure selected from N-piperidinyl, N-pyrrolidinyl, N-morpholinyl, and N-hexamethyleneimino; each $R^1$ is independently hydrogen, hydroxy, halogen or methoxy; and pharmaceutically acceptable salts and solvates thereof.

U.S. Pat. No. 4,536,516 describes Tamoxifene, a triarylethylene having the formula

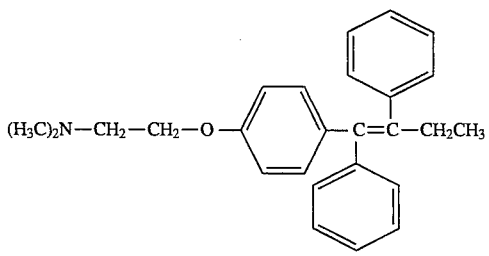

Ia and pharmaceutically acceptable acid addition salts and solvates thereof, and discloses methods of synthesis.

Similarly, U.S. Pat. No. 2,914,563 describes triarylethylenes having the formula

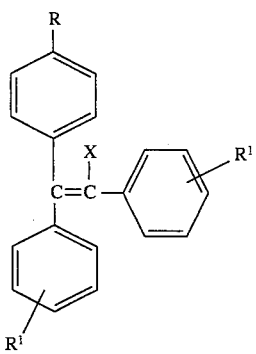

II where

R is a basic ether group of the formula —$OC_nH_{2n}A$ where n is 2,3 or 4 and A is a dialkylamino group where the alkyl groups independently contain from 1 to 4 carbon atoms or a cyclic structure such as N-piperidinyl, N-pyrrolidinyl or N-morpholinyl group. The group —$OC_nH_{2n}A$ is bonded to the phenyl ring para to the carbon atom bonded to the ethylene group. Each $R^1$ is independently hydrogen, hydroxy, halogen or methoxy; X is halogen; and pharmaceutically acceptable salts and solvates thereof. Methods of synthesizing these compound are disclosed therein.

In Ogawa et al., supra, triarylethylenes are disclosed having the formula

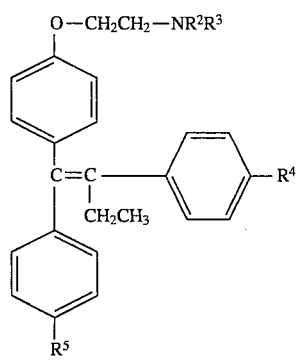

III where $R^2$ and $R^3$ are independently selected from hydrogen and methyl;

$R^4$ is isopropyl, isopropen-2-yl, or mono or dihydroxy isopropyl;

$R^5$ is hydroxy or phosphate (—$OPO_3H_2$); and pharmaceutically acceptable salts and solvates thereof. This article also discloses synthesis of these compounds.

A second class of antiestrogens comprises the 2,3- diaryl-2H-1-benzopyrans. These compounds are disclosed in and prepared according to procedures described in EP 470 310A1, and Sharma, et al., *J. Med. Chem.*, 33. 3210, 3216, 3222 (1990) which are incorporated by reference herein in their entirety. Specific illustrative compounds within this class include 2-[4-[2-(1-piperidinyl)ethoxy]phenyl]-3-[4-hydroxyphenyl]-2H-1-benzopyran; 2-[4-[2-(1-piperidinyl)ethoxy]phenyl]-3-phenyl-7-methoxy-2H-1-benzopyran; 2-[4-[2-(1-piperidinyl)ethoxy]phenyl]-3-[4-hydroxyphenyl] -7-hydroxy-2H-1-benzopyran.

EP 470 310 A1 describes benzopyrans having the formula

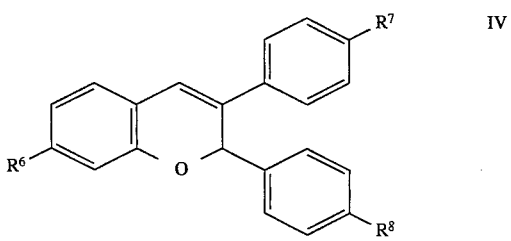

IV where $R^6$ and $R^7$ are the same or different hydrogen hydroxy, $C_1$-$C_{17}$ alkoxy or $C_2$-$C_{18}$ alkoxycarbonyl;

$R^8$ is

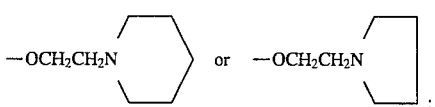

and pharmaceutically acceptable salts and solvates thereof. Synthesis of these benzopyrans is described therein.

A third class of antiestrogens comprises the 1-aminoalkyl-2-phenylindoles. These compounds are disclosed in and prepared according to procedures described in von Angerer, et al., *J. Med. Chem.* 33, 2635 (1990) which is incorporated by reference herein in its entirety.

The 1-aminoalkyl-2-phenylindoles described in yon Angerer et al., supra, are those having the formula

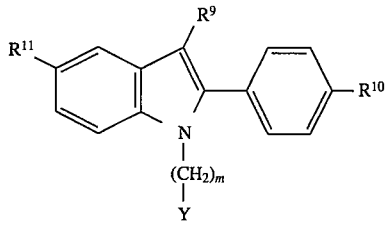

V where
 $R^9$ is hydrogen or methyl;
 $R^{10}$ and $R^{11}$ are methoxy or hydroxy;
 m is 4 to 8;
 Y is $NR^{12}R^{13}$ where $R^{12}$ and $R^{13}$ are independently selected from hydrogen, methyl and ethyl or one of $R^{12}$ or $R^{13}$ is hydrogen and the other is benzyl or are combined with the nitrogen atom to constitute a pyrrolidinyl, piperidinyl or morpholinyl group,
and pharmaceutically acceptable salts and solvates thereof.

Procedures for synthesing these compound are specifically disclosed or referenced therein.

A fourth class of antiestrogens comprises the 2-phenyl-3-aroylbenzo[b]thiophenes; (Z-triarylpropenones). These compounds are disclosed in and prepared according to procedures described in U.S. Pat. No. 4,133,814; U.S. Pat. No. 4,418,068; and Jones, et al., *J. Med. Chem.*, 27, 1057–1066 (1984) which are all incorporated by reference herein in their entirety. Specific illustrative compounds within this class include Raloxifene [6-hydroxy-2-(4hydroxyphenyl)benzo[b]thien-3 -yl][4-[2-(1piperidinyl)ethoxy] phenyl]methanone hydrochloride, formerly keoxifene; and [6-hydroxy-2-(4-hydroxyphenyl)benzo[b]thien-3yl][4-[2-(1-pyrrolidinyl)ethoxy]phenyl]methanone Hydrochloride.

The 2-phenyl-3-aroylbenzo[b]thiophenes are exemplified by those in U.S. Pat. No. 4,133,814 and have the formula

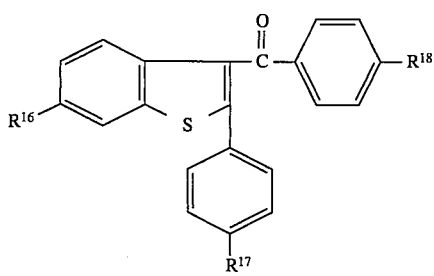

VI where
 $R^{16}$ is hydrogen, hydroxy, $C_1$–$C_5$ alkoxy, $C_1$–$C_7$ alkanoyloxy, $C_3$–$C_7$ cycloalkanoyloxy, ($C_1$–$C_6$ alkoxy)-$C_1$–$C_7$ alkanoyloxy, substituted or unsubstituted aroyloxy, or substituted or unsubstituted aryloxycarbonyloxy;
 $R^{17}$ is hydrogen, hydroxy, $C_1$–$C_5$ alkoxy, adamantoyloxy, chloro, bromo, $C_1$–$C_7$ alkanoyloxy, $C_3$–$C_7$ cycloalkanoyloxy, ($C_1$–$C_6$ alkoxy)-$C_1$–$C_7$ alkanoyloxy, substituted or unsubstituted aroyloxy, or substituted or unsubstituted aryloxycarbonyloxy;
 $R^{18}$ is —O—$CH_2$—$CH_2$—X'$NR^{19}R^{20}$; X' is a bond or —$CH_2$—, $R^{19}$ and $R^{20}$ are independently $C_1$–$C_4$ alkyl or are taken together with the nitrogen atom to which they are bonded to constitute a pyrrolidinyl, piperidinyl, hexamethyleneiminyl, or morpholinyl ring; and pharmaceutically acceptable acid addition salts and solvates thereof.

Methods of synthesizing these compounds are disclosed in U.S. Pat. No. 4,133,814. Raloxifene, and its preparation are described in U.S. Pat. No. 4,418,068.

A fifth class of antiestrogens comprises the 1-substituted-2-aryl-dihydronaphthalenes. These compounds are disclosed in and prepared according to procedures described in U.S. Pat. Nos. 4,400,543; 4,323,707; 4,230,862; and 3,274,213 which are all incorporated by reference herein in their entirety. Specific illustrative compounds within this class include Nafoxidene and Trioxifene.

The 1-substituted-2-aryl-dihydronaphthalenes are exemplified by U.S. Pat. No. 4,230,862 that describes compounds having the formula:

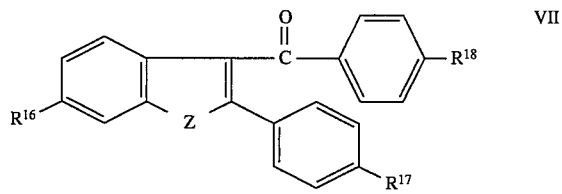

VII where
 Z is —$CH_2$—$CH_2$— or —CH=CH—;
 $R^{16}$ is hydrogen, hydroxy or $C_1$–$C_5$ alkoxy;
 $R^{17}$ is hydrogen, hydroxy, $C_1$–$C_5$ alkoxy, $C_1$–$C_5$ acyloxy, $C_1$–$C_5$ alkoxycarbonyloxy, benzyloxy, adamantoyloxy, chloro, or bromo
 $R^{18}$ is $C_1$–$C_5$ alkoxy or —O—$CH_2$—$CH_2$—$NR^{19}R^{20}$; and $R^{19}$ and $R^{20}$ are independently $C_1$–$C_4$ alkyl or are taken together with the nitrogen atom to which they are bonded to constitute a pyrrolidinyl, piperidinyl, hexamethyleneimino, or morpholinyl ring; subject to the limitation that when $R^{17}$ is hydrogen, $R^{16}$ is hydrogen, hydroxy, or $C_1$–$C_5$ alkoxy and at least one of $R^{16}$ and $R^{17}$ is other than hydrogen; and pharmaceutically acceptable acid addition salts and solvates thereof.

Methods of synthesizing these compound are disclosed in U.S. Pat. No. 4,230,862.

The 1-substituted-2-aryl-dihydronaphthalenes are also exemplified by U.S. Pat. No. 3,274,213 that describes compounds having the formula

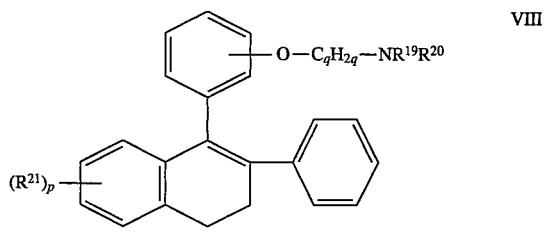

VIII where
 $R^{19}$ and $R^{20}$ are $C_1$–$C_8$ alkyl or are taken together with the nitrogen atom to which they are bonded to form a 5 to 7 membered saturated heterocyclic radical selected from pyrrolidinyl, 2-methylpyrrolidinyl, 2,2dimethylpyrrolidinyl, piperazinyl, 4-methylpiperazinyl, 2,4-dimethylpiperazinyl, morpholinyl, piperidinyl, 2-methylpiperidinyl, 3-methylpiperidinyl, hexamethyleneiminyl, homopiperazinyl, and homomorpholinyl;
 q is 2 to 6;
 p is 1 to 4;
 $R^{21}$ is $C_1$–$C_8$ alkoxy; and pharmaceutically acceptable salts and solvates thereof.

Methods of synthesizing these compounds are disclosed therein.

A sixth class of antiestrogens comprises the 2-substituted-3-aryl-benzofurans. These compounds are disclosed in and prepared according to procedures described in Teo et al., *J. Med. Chem.*, 35, 1330–1339 which is incorporated by reference herein in its entirety.

The 2-substituted-3-aryl-benzofurans described in Teo em al., *J. Med. Chem.*, 35, 1330–1339 (1992) includes hose having the formula

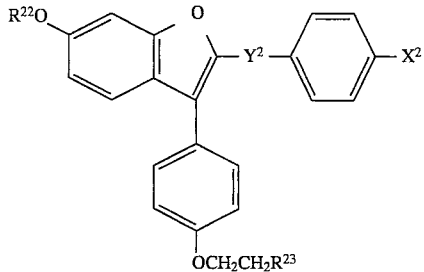

where $X^2$ is halo;

$y^2$ is a bond or $-CH_2-$;

$R^{22}$ is hydrogen or methyl;

$R^{23}$ is a group $-NR^{19}R^{20}$, where $R^{19}$ and $R^{20}$ are independently $C_1-C_4$ alkyl or are taken together with the nitrogen atom to which they are bonded to constitute a pyrrolidinyl, piperidinyl, hexamethyleneiminyl or morpholinyl ring; and pharmaceutically acceptable salts and solvates thereof.

Methods of synthesizing these compound are also disclosed therein.

The preferred class of compounds useful in the methods of the present invention are the benzothiophenes. More preferred are benzothiopenes having the formula:

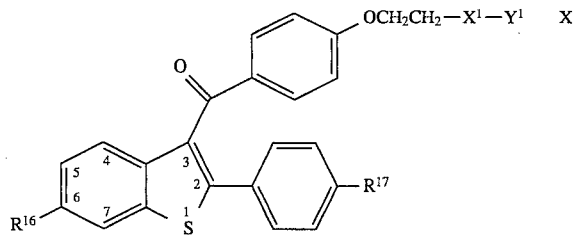

wherein $X^1$ is a bond or $-CH_2-$;

$R^{16}$ is hydroxyl, methoxy, $C_1-C_7$ alkanoyloxy, $C_3-C_7$ cycloalkanoyloxy, (C1–$C_6$ alkoxy)-C1–$C_7$ alkanoyloxy, substituted or unsubstituted aroyloxy, or substituted or unsubstituted aryloxycarbonyloxy;

$R^{17}$ is hydrogen, hydroxyl, chloro, bromo, methoxy, $C_1-C_7$ alkanoyloxy, $C_3-C_7$ cycloalkanoyloxy, (C1–$C_6$ alkoxy)-C1–$C_7$ alkanoyloxy, substituted or unsubstituted aroyloxy, or substituted or unsubstituted aryloxycarbonyloxy;

$y^1$ is a heterocyclic ring selected from the group consisting of pyrrolidinyl, piperidinyl, or hexamethyleneiminyl; and pharmaceutically acceptable salts and solvates thereof. Particularly preferred are Raloxifene and its pyrrolidinyl analog.

The present invention provides a method for lowering blood glucose levels in mammals comprising administering a therapeutically effective amount of an antiestrogen compound or a pharmaceutically acceptable salt or solvate thereof. The term "therapeutically effective amount", as defined herein, means the amount of compound necessary to provide a hypoglycemic effect following administration, preferably to a human suffering from or susceptible to adult onset diabetes. The hypoglycemic effect contemplated by the present method includes both medical therapeutic and/or prophylactic treatment, as appropriate. Also contemplated as within the scope of the present invention is concomitant treatment with oral hypoglycemic agents, insulin or an insulin derivative. Such additional therapeutic agents would be determined by the attending physician as circumstances dictate.

The hypoglycemic activity of the compounds of the present invention was determined by testing the efficacy of the compounds in vivo in male viable yellow obese-diabetic mice. The test procedure is described below.

Five to 6 month old male, inbred viable yellow obese-diabetic mice (VY/WfL-$A^{vy}$/a, referred to as diabetic mice) from the Lilly colony were used. The VY strain carrying the $A^{vy}$ mutation was transferred from Dr. George L. Wolff to Lilly Research Laboratories about 20 years ago. The colony has been maintained by sister×brother inbreeding between $A^{vy}$/a and a/a mice. Male viable yellow mice are obese, hyperglycemic, hyperinsulinemic and insulin resistant.

Mice were housed 6 per plastic cage with bedding and fed water and Purina Formulab Chow 5008 (Purina Mills, St. Louis, Mo.) ad libitum. The temperature of the animal rooms was maintained at 23 ±2° C. Lights in the animal rooms were on from 0600 to 1800 h.

Antiestrogens were tested at various doses as admixtures of diets. Each dose of an antiestrogen was tested on 6 mice housed in the same cage. Compounds were mixed in pulverized chow and repelletized. Mice serving as controls were given repelletized diet without any test compound. Blood samples were collected from the tail vein immediately before and weekly after the start of a test. Blood glucose concentrations were determined by the glucose oxidase method with a model 300 Alpkem Rapid Flow Analyzer (Clackamaus, Oreg.).

The values reported in Tables 1, 2 and 3 are the mean average obtained in each test, while each Table reports a separate test. Doses are average doses based upon actual food consumption and body weight. Table 2 reports the results on ICI 164384, an antiestrogen having substantially no estrogenic activity and is outside the scope of the present invention. Statistical analysis of data was by the least significant difference method based on an analysis of variance.

TABLE 1

HYPOGLYCEMIC ACTIVITY OF TEST COMPOUNDS IN OBESE DIABETIC MICE

| Compound Tested | Dose (mg/kg/day) | Blood Glucose Concentration (mg/dl) | | |
|---|---|---|---|---|
| | | 0 days | 7 days | 14 days |
| Tamoxifen | 0.08 | 483 ± 15 | 280 ± 42 | 288 ± 28 |
| | 0.20 | 466 ± 31 | 194 ± 29 | 196 ± 23 |
| | 0.74 | 533 ± 16 | 240 ± 32 | 188 ± 20 |
| | 2.30 | 450 ± 39 | 183 ± 22 | 207 ± 26 |
| Trioxifene | 0.09 | 483 ± 20 | 223 ± 26 | 234 ± 32 |
| | 0.27 | 501 ± 13 | 192 ± 27 | 164 ± 14 |
| | 0.88 | 471 ± 32 | 186 ± 27 | 158 ± 12 |
| | 2.00 | 501 ± 32 | 154 ± 24 | 141 ± 4 |
| Untreated Control | 0.02 | 543 ± 31 | 457 ± 27 | 434 ± 9 |

TABLE 2

HYPOGLYCEMIC ACTIVITY OF TEST COMPOUNDS IN OBESE DIABETIC MICE

| Compound Tested | Dose (mg/kg/day) | Blood Glucose Concentration (mg/dl) | | |
|---|---|---|---|---|
| | | 0 days | 7 days | 14 days |
| ICI 164384 | 0.03 | 366 ± 17 | 326 ± 21 | 317 ± 30 |
| N-n-butyl-N-methyl-11-(3,17β-dihydroxyestra-1,3,5(10)-trien-7α-yl)undecamide | 0.30 | 381 ± 18 | 388 ± 16 | 327 ± 14 |
| | 2.80 | 383 ± 27 | 292 ± 26 | 297 ± 15 |
| [6-hydroxy-2-(4-hydroxyphenyl)-benzo[b]thien-3-yl][4-[2-(1-pyrrolidinyl)ethoxy]phenyl]-methanone hydrochloride | 0.03 | 354 ± 13 | 361 ± 14 | 318 ± 15 |
| | 0.24 | 327 ± 20 | 250 ± 33 | 210 ± 26 |
| | 1.95 | 379 ± 18 | 185 ± 44 | 163 ± 32 |
| 17α-ethynylestradiol | 0.02 | 400 ± 17 | 108 ± 3 | 105 ± 2 |

TABLE 3

HYPOGLYCEMIC ACTIVITY OF TEST COMPOUNDS IN OBESE DIABETIC MICE

| Compound Tested | Dose (mg/kg/day) | Blood Glucose Concentration (mg/dl) | | |
|---|---|---|---|---|
| | | 0 days | 7 days | 14 days |
| Raloxifene | 0.1 | 363 ± 23 | 354 ± 16 | 357 ± 11 |
| | 0.28 | 406 ± 20 | 378 ± 17 | 314 ± 11 |
| | 0.84 | 373 ± 34 | 239 ± 39 | 196 ± 35 |
| | 2.4 | 407 ± 14 | 231 ± 34 | 165 ± 32 |
| | 7.36 | 390 ± 10 | 210 ± 26 | 177 ± 25 |
| 17α-ethynylestradiol | 0.025 | 399 ± 10 | 186 ± 10 | 151 ± 14 |

The following procedures describe the preferred methods of determining the estrogenic/antiestrogenic activities of the compounds described above.

Femur Density

Seventy-five day old female Sprague Dawley rats (weight range of 225 to 275 g) are obtained from Charles River Laboratories (Portage, Mich.). They are housed in groups of 3 and have ad libitum access to food (calcium content approximately 1%) and water. Room temperature is maintained at 22.2°±1.7° C. with a minimum relative humidity of 40%. The photoperiod in the room is 12 hours light and 12 hours dark.

One week after arrival, the rats undergo bilateral ovariectomy under anesthesia (44 mg/kg Ketamine and 5 mg/kg Xylazine (Butler, Indianapolis, Ind.) administered intramuscularly). Treatment with vehicle, estrogen, or a test compound is initiated on the day of surgery following recovery from anesthesia. Oral dosage is by gavage in 0.5 mL of 1% carboxymethylcellulose (CMC) or 20% cyclodextrin. Body weight is determined at the time of surgery and weekly thereafter and the dosage is adjusted with changes in body weight. Vehicle or estrogen treated ovariectomized (ovex) rats and non-ovariectomized (intact) rats are evaluated in parallel with each experimental group to serve as negative and positive controls.

The rats are treated daily for 35 days (6 rats per treatment group) and sacrificed by carbon dioxide asphyxiation on the 36th day. The 35 day time period is sufficient to allow maximal reduction in bone density in ovariectomized rat, measured as described herein. At the time of sacrifice, the uteri are removed, dissected free of extraneous tissue, and the fluid contents are expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and scanned at the distal metaphysis 1 mm from the patellar groove with single photon absorptiometry. Results of the densitometer measurements represent a calculation of bone density as a function of the bone mineral content and bone width.

Ovariectomy of the rats causes a reduction in femur density of about 25% as compared to intact vehicle treated controls. Estrogen, administered in the orally active form of ethynyl estradiol ($EE_2$), prevents this loss of bone in a dose dependent manner, but it also exerts a stimulatory action on the uterus resulting in uterine weights approaching that of an intact rat when administered at 100 µg/kg.

Uterus Histological Parameters

Increases in epithelial height are a sign of estrogenicity of therapeutic agents and may be associated with increased incidence of uterine cancer. Increase in epithelial height over the ovariectomized controls are compared. Estradiol treatment increases epithelial height to a thickness greater than intact rats.

Estrogenicity is also assessed by evaluating the adverse response of eosinophil infiltration into the stromal layer of the uterus. Estradiol, as expected, causes a large increase in eosinophil infiltration.

Thickness of the stroma and myometrium are also measured. Estrogen causes an increase in both of these parameters.

A total score of estrogenicity, is a compilation of all four parameters.

Some data may be reported as percent inhibition of bone loss and percent uterine weight gain which are calculated as follows:

Percent inhibition of bone loss equals (bone density of treated ovex animals—bone density of untreated ovex animals)÷(bone density of estrogen treated ovex animals—bone density of untreated ovex animals) ×100.

Percent uterine weight gain equals (uterine weight of treated ovex animals—uterine weight of ovex animals)÷(uterine weight of estrogen treated ovex animals—uterine weight of ovex animals)×100.

Serum Lipid Levels

Seventy-five day old female Sprague Dawley rats {weight range of 200 to 225 g) are obtained from Charles River Laboratories (Portage, Mich.). The animals are either bilaterally ovariectomized (OVX) or exposed to a Sham surgical procedure at Charles River Laboratories, and then shipped after one week. Upon arrival, they are housed in metal hanging cages in groups of 3 or 4 per cage with ad libitum access to food (calcium content approximately 0.5%) and water for one week. Room temperature is maintained at 22.2°±1.7° C. with a minimum relative humidity of 40%. The photoperiod in the room is 12 hours light and 12 hours dark.

Dosing Regimen/Tissue Collection

After a one week acclimation period (therefore, two weeks post-OVX) daily dosing with test compound is initiated. All compounds are administered orally at 1 ml/kg body weight. 17β-Estradiol is administered subcutaneously in a 20% polyethylene glycol vehicle, 17α-ethynyl estradiol and the test compound are given orally as a suspension in 1% carboxymethylcellulose or 20% cyclodextrin. Animals are dosed daily for 4 days. Following the dosing regimen animals are weighed and anesthetized with a ketamine: Xylazine (2:1, (V:V) mixture and a blood sample collected by cardiac puncture. The animals are then sacrificed by asphyxiation with $CO_2$ and the uterus removed through a midline incision and a wet weight determined.

Cholestrol Analysis

Blood samples are allowed to clot at room temperature for 2 hrs, and serum is obtained following centrifugation for 10 min at 3000 rpm. Serum cholesterol is determined using a Boehringer Mannhelm Diagnostics high performance cholesterol assay. Briefly, the cholesterol is oxidized to cholest-4-en-3-one and hydrogen peroxide. The hydrogen peroxide was then reacted with phenol and 4-aminophenazone in the presence of peroxidase to produce a p-quinone imine dye, which is read spectrophotemetrically at 500 nm. Cholesterol concentration is then calculated against a standard curve. The entire assay is automated using a Biomek Automated Workstation.

Uterine Eosinophil Peroxidase (EPO) Assay

Uteri are kept at 4° C. until time of enzymatic analysis. The uteri are then homogenized in 50 volumes of 50 mM Tris buffer (pH - 8.0) containing 0.005% Triton X-100. Upon addition of 0.01% hydrogen peroxide and t0 mM o-phenylenediamine (final concentrations) in Tris buffer, increase in absorbance is monitored for one minute at 450 rim. The presence of eosonophils in the uterus is an indication of estrogenic activity of a compound. The maximal velocity of a 15 second interval is determined over the initial, linear portion of the reaction curve.

Experimental Groups

All experimental groups are comprised of five or six animals.

Ovariectomy of the rats caused an increase in serum cholesterol as compared to intact vehicle treated controls. Estrogen, administered in the orally active form of ethynyl estradiol ($EE_2$), causes a decrease in serum cholesterol in a dose dependent manner, but it also exerts a stimulatory action on the uterus resulting in uterine weights approaching that of an intact rat when administered at 100 µg/kg/day.

Histological Parameters

Histological evaluations are carried out as described above.

Inhibitory activity of compounds as to estrogen dependent mammary tumors are evaluated according to procedures described in U.S. Pat. Nos. 4,133,814 and 4,418,068. The compounds utilized in the method of the present invention are effective over a wide dosage range. For example, dosages per day will normally fall within the range of about 10 to about 1000 mg/kg of body weight. In the treatment of adult humans, the range of about 50 to about 600 mg/kg, in single or divided doses, is preferred. However, it will be understood that the amount of the compound actually administered will be determined by a physician in light of the relevant circumstances including the condition to be created, the choice of compound to be administered, the age, weight, and response of the individual patient, the severity of the patient's symptoms and the chosen route of administration. Therefore, the above dosage ranges are not intended to limit the scope of the invention in any way. While the present compounds are preferably administered orally, the compounds may also be administered by a variety of other routes such as the transdermal, subcutaneous, intranasal, intramuscular and intravenous routes.

While it is possible to administer a compound of the invention directly, the compounds are preferably employed in the form of a pharmaceutical formulation comprising a pharmaceutically acceptable carrier, diluent or excipient and a compound of the invention. Such formulations will contain from about 0.01 percent to about 99 percent of a compound of the invention.

In making the formulations of the present invention, the active ingredient will usually be mixed with at least one carrier, or diluted by at least one carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the formulations can be in the form of tablets, granules, pills, powders, lozenges, sachets, cachets, elixirs, emulsions, solutions, syrups, suspensions, aerosols (as a solid or in a liquid medium) and soft and hard gelatin capsules.

Examples of suitable carriers, diluents and excipients include lactose, dextrose, sucrose, sorbitol, mannitol, starches, gum acacia, calcium phosphate, alginates, liquid paraffin, calcium silicate, microcrystalline cellulose, polyvinyl pyrrolidone, cellulose, tragacanth, gelatin, syrup, methyl cellulose, methyl- and propyl-hydroxybenzoates, vegetable oils, such as olive oil, injectable organic esters such as ethyl oleate, talc, magnesium stearate, water and mineral oil. The formulations may also include wetting agents, lubricating, emulsifying and suspending agents, preserving agents, sweetening agents, perfuming agents, stabilizing agents or flavoring agents. The formulations of the invention may be formulated so as to provide quick, sustained or delayed release of the active ingredient after administration to the patient by employing procedures well-known in the art.

For oral administration, a compound of this invention ideally can be admixed with carriers and diluents and molded into tablets or enclosed in gelatin capsules.

The compositions are preferably formulated in a unit dosage form, each dosage containing from about 1 to about 500 mg, more usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier, diluent or excipient therefor.

In order to more fully illustrate the operation of this invention, the following examples of formulations are provided. The examples are illustrative only and are not intended to limit the scope of the invention. The formulations may employ as active compounds any of the antiestrogen compounds described above.

FORMULATION 1
Hard gelatin capsules are prepared using the following ingredients:

| | Amt. per Capsule | Concentration by Weight (percent) |
|---|---|---|
| Active Ingredient | 250 mg | 55.0 |
| Starch dried | 220 mg | 43.0 |
| Magnesium stearate | 10 mg | 2.0 |
| | 460 mg | 100.0 |

The above ingredients are mixed and filled into hard gelatin capsules in 460 mg quantities.

FORMULATION 2
Capsules each containing 20 mg of medicament are made as follows:

| | Amt. per Capsule | Concentration by Weight (percent) |
|---|---|---|
| Active Ingredient | 20 mg | 10.0 |
| Starch | 89 mg | 44.5 |
| Microcrystalline cellulose | 89 mg | 44.5 |
| Magnesium stearate | 2 mg | 1.0 |
| | 200 mg | 100.0 |

The active ingredient, cellulose, starch and magnesium stearate are blended, passed through a No. 45 mesh U.S. sieve and filled into a hard gelatin capsule.

FORMULATION 3
Capsules each containing 100 mg of active ingredient are made as follows:

| | Amt. per Capsule | Concentration by Weight (percent) |
|---|---|---|
| Active ingredient | 100 mg | 29.0 |
| Polyoxyethylenesorbitan monooleate | 50 mcg | 0.02 |
| Starch powder | 250 mg | 71.0 |
| | 250.05 mg | 100.02 |

The above ingredients are thoroughly mixed and placed in an empty gelatin capsule.

FORMULATION 4
Tablets each containing 10 mg of active ingredient are made up as follows:

| | Amt. per Capsule | Concentration by Weight (percent) |
|---|---|---|
| Active Ingredient | 10 mg | 10.0 |
| Starch | 45 mg | 45.0 |
| Microcrystalline cellulose | 35 mg | 35.0 |
| Polyvinyl pyrrolidone (as 10% solution in water) | 4 mg | 4.0 |
| Sodium carboxyethyl starch | 4.5 mg | 4.5 |
| Magnesium stearate | 0.5 mg | 0.5 |
| Talc | 1 mg | 1.0 |
| | 100 mg | 100.0 |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granule so produced is dried at 50°–60° C. and passed through a No. 18 mesh U.S. sieve. The sodium carboxymethyl starch, magnesium stearate and talc, previously passed through a No. 60 mesh U.S. sieve, are then added to the granule which, after mixing, is compressed on a tablet machine to yield a tablet weighing 100 mg.

FORMULATION 5
A tablet formula may be prepared using the ingredients below:

| | Amt. per Capsule | Concentration by Weight (percent) |
|---|---|---|
| Active Ingredient | 250 mg | 38.0 |
| Cellulose microcrystalline | 400 mg | 60.0 |
| Silicon dioxide fumed | 10 mg | 1.5 |
| Stearic acid | 5 mg | 0.5 |
| | 665 mg | 100.0 |

The components are blended and compressed to form tablets each weighing 665 mg.

FORMULATION 6
Suspensions each containing 5 mg of medicament per 40 ml dose are made as follows:

| | Per 5 ml of suspension |
|---|---|
| Active Ingredient | 5 mg |
| Sodium carboxymethyl cellulose | 50 mg |
| Syrup | 1.25 ml |
| Benzoic acid solution | 0.10 ml |
| Flavor | q.v. |
| Color | q.v. |
| Water | q.s. to 5 ml |

The medicament is passed through a No. 45 mesh U.S. sieve and mixed with the sodium carboxymethylcellulose and syrup to form a smooth paste. The benzoic acid solution, flavor and color is diluted with some of the water and added, with stirring. Sufficient water is then added to produce the required volume.

FORMULATION 7
An aerosol solution is prepared containing the following components:

| | Concentration by Weight (%) |
|---|---|
| Active Ingredient | 0.25 |
| Ethanol | 29.75 |
| Propellant 22 (Chlorodifluoromethane) | 70.00 |
| | 100.00 |

The active compound is mixed with ethanol and the mixture added to a portion of the propellant 22, cooled to −30° C. and transferred to a filling device. The required amount is then fed to a stainless steel container and diluted further with the remaining amount of propellant. The valve units are then fitted to the container.

We claim:

1. A method of reducing blood glucose concentration in mammals which comprises administering to a mammal in need of treatment [6-hydroxy-2-(4-hydroxyphenyl)benzo[b]thien-3-yl][4-[2-(1-piperidinyl)ethoxy]phenyl]methanone and pharmaceutically acceptable salts and solvates thereof.

2. The method as recited in claim 1 wherein said mammal is a human.

3. A method of reducing blood glucose concentration in mammals which comprises administering to a mammal in need of treatment [6-hydroxy-2-(4-hydroxphenyl)benzo[b]thien-3-yl][4-[2-(1-pyrrolidinyl)ethoxy[phenyl[methanone and pharmaceutically acceptable salts and solvates thereof.

4. The method as recited in claim 3 wherein said mammal is a human.

* * * * *